United States Patent [19]

Sommer et al.

[11] 4,100,067
[45] Jul. 11, 1978

[54] METHOD FOR SEQUESTERING METAL IONS

[75] Inventors: Klaus Sommer, Heidelberg; Günter Raab, Laudenbach, Bergstr., both of Fed. Rep. of Germany

[73] Assignee: Benckiser-Knapsack GmbH., Ladenburg am Neckar, Fed. Rep. of Germany

[21] Appl. No.: 760,367

[22] Filed: Jan. 18, 1977

Related U.S. Application Data

[62] Division of Ser. No. 675,479, Apr. 9, 1976, Pat. No. 4,029,696.

[51] Int. Cl.$^2$ ............................................. C02B 5/06
[52] U.S. Cl. ................................. 210/58; 21/2.7 A; 252/180; 252/389 A; 252/390; 162/76; 162/80; 162/158; 162/DIG. 4
[58] Field of Search .............. 21/2.7 A; 210/54, 58, 210/59; 252/180, 181, 8.55 E, 389 A, 390; 260/502.5; 162/76, 80, 158, DIG. 4

[56] References Cited

U.S. PATENT DOCUMENTS

| | | | |
|---|---|---|---|
| 2,917,528 | 12/1959 | Ramsey et al. | 260/502.5 |
| 2,964,549 | 12/1960 | Ramsey et al. | 260/502.5 |
| 3,733,270 | 5/1973 | Kerst | 210/58 |
| 3,904,493 | 9/1975 | Losi et al. | 260/502.5 |
| 3,907,652 | 9/1975 | Wagenknecht et al. | 260/502.5 |
| 3,957,160 | 5/1976 | Plöger et al. | 210/58 |
| 4,010,067 | 3/1977 | Hoeger et al. | 162/DIG. 4 |
| 4,029,696 | 6/1977 | Sommer et al. | 210/58 |
| 4,029,697 | 6/1977 | Krueger et al. | 210/58 |
| 4,054,598 | 10/1977 | Blum et al. | 210/58 |
| 4,056,430 | 11/1977 | Hoeger et al. | 162/DIG. 4 |

FOREIGN PATENT DOCUMENTS

| | | | |
|---|---|---|---|
| 7,200,995 | 8/1972 | Netherlands | 210/58 |

*Primary Examiner*—Charles N. Hart
*Assistant Examiner*—Peter A. Hruskoci
*Attorney, Agent, or Firm*—Bacon & Thomas

[57] ABSTRACT

Valuable amino alkane diphosphonic acids in which one or both hydrogen atoms of the amino group are substituted by hydroxy alkane groups, and their alkali metal salts and a process of using them are described. Said compounds are highly water-soluble, are stable against hydrolysis even at temperatures exceeding 100° C., and have a high sequestering power so that they can be used advantageously, for instance, in processing aqueous media of considerable hardness, and in suppressing scale and corrosion in aqueous media used for heat treatment of containers.

3 Claims, No Drawings

METHOD FOR SEQUESTERING METAL IONS

This is a division, of application Ser. No. 675,479, filed Apr. 9, 1976, now U.S. Pat. No. 4,029,696.

BACKGROUND OF THE INVENTION (1) Field of the Invention

The present invention relates to novel amino alkane diphosphonic acids and more particularly to novel N-hydroxy alkane amino alkane diphosphonic acids and their alkali metal salts, to a process of making said compounds, to compositions containing them, and to a method of using such compositions.

(2) Description of the Prior Art

Only a limited number of hydroxy amino phosphonic acids are known at present. For instance, German Pat. No. 1,214,229 describes, among others, the production of mono-ethanolamino or, respectively, di-ethanolamino (methyl phosphonic acids). These compounds are produced by phosphono-methylating mono-ethanolamine or, respectively, di-ethanolamine by means of phosphorous acid and formaldehyde. Hydroxy amino (methyl phosphonic acids) in which one or two methylene phosphonic acid groups ($-CH_2PO_3H_2$) are attached to the nitrogen atom, are obtained according to the process of said patent.

German Published Application (Auslegeschrift) No. 2,130,794 relates to a process of producing 1-hydroxy-3-amino propane-1,1-diphosphonic acid by reacting β-alanine with phosphorus trichloride and phosphorous acid. The resulting reaction product is a hydroxy amino diphosphonic acid in which no substituent is attached to the amino group, while the hydroxyl group is attached to the same carbon.

An object of the present invention is to provide a method of using N-hyroxy alkane amino alkane diphosphonic acids for complex formation and sequestering effects in aqueous media.

Another object of the present invention is to provide a method of using N-hydroxy alkane amino alkane diphosphonic acids for suppressing scale and corrosion in an aqueous medium used for the heat treatment of containers.

Other objects of the present invention will become apparent as the description proceeds.

In principle the novel N-hydroxy alkane amino alkane diphosphonic acids according to the present invention are represented by the following formula

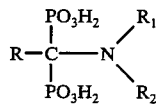

In said formula

R is hydrogen, lower alkyl, especially methyl or ethyl; aryl, especially phenyl; hydroxy alkyl, especially hydroxy ethyl; or carboxy alkyl, especially carboxy methyl;

$R_1$ is hydrogen; lower alkyl, especially methyl; hydroxy alkyl, especially hydroxy alkyl of the formula $C_nH_{2n}OH$; the propylene glycol group of the formula $C_3H_7O_2$; or the hydroxy propionic acid group of the formula $C_3H_5O_3$; and $R_2$ is hydroxy alkyl, especially hydroxy alkyl of the formula $C_nH_{2n}OH$;

$n$ in said hydroxy alkyl group is a numeral from 2 and 3.

It is evident that the novel phosphonic acids according to the present invention differ from the known hydroxy amino phosphonic acids disclosed in the above mentioned German Patent and German Published Application by the feature that geminate phosphonic acid groups are present at the $C_1$-atom. In contrast to the 1-hydroxy-3-amino propane-1,1-diphosphonic acid disclosed in German Published Application No. 2,130,794 the substituents carrying the hydroxyl groups are attached to the nitrogen atom of the amino group while, according to said German Published Application, the amino group is not substituted.

The phosphonic acids according to the present invention or their alkali metal salts are preferably obtained by reacting amino alkane diphosphonic acids with one or two hydrogen atoms at their nitrogen atom with three- and four-membered cyclic ethers. Suitable cyclic ethers are, for instance, ethylene oxide, propylene oxide, trimethylene oxide, glycidol and its ethers, epichlorohydrin, glycidic acid and its esters and amides, β-methyl glycidic acid and its esters and amides, and the like cyclic ethers.

Especially suitable phosphonic acids starting materials are amino lower alkane diphosphonic acids having up to four carbon atoms in the alkane chain and also amino aryl alkane diphosphonic acids. Examples of such phosphonic acids are, for instance, amino methane diphosphonic acid, amino ethane diphosphonic acid, 2-carboxy-1-amino ethane-1,1-diphosphonic acid, benzylamino diphosphonic acid, 1-amino propane-1,1-diphosphonic acid, and the like.

The reaction components, i.e. the amino alkane phosphonic acids and the cyclic ethers, are advantageously reacted in the proportion of 1 : 1 to 1 : 1.5, if only one replaceable hydrogen atom is attached to the nitrogen atom, or in the proportion of 1 : 2 to 1 : 3, if both hydrogen atoms of the amino group of the starting phosphonic acid can be replaced.

Preferably the sodium and potassium salts of the starting phosphonic acids are used in the reaction. The free amino phosphonic acids themselves, however, can also be used under certain conditions, although the preferred procedure is to use the alkali metal salts in the reaction. When using the free acids, it is the preferred procedure to carry out the reaction in the presence of an alkali metal hydroxide.

The resulting new phosphonic acids are distinguished over known phosphonic acids by being readily prepared in a good yield and by being of a water-solubility that can be considered as excellent for most uses. The new phosphonic acids are highly effective agents for yielding complex compounds with divalent and polyvalent metal ions. They can be employed advantageously in all those instances in which a high sequestering power is required.

The novel phosphonic acids according to the present invention have proved to be especially valuable, because they are highly stable against hydrolysis even at a high temperature. Thus they can be employed in all those processes in which the temperature exceeds 100° C. and they can be used in all aqueous media in which the hardness-forming agents in the water have a disturbing or detrimental effect or in which the action of polyvalent metal ions is to be excluded.

The new phosphonic acids have proved to be of value for stabilizing the hardness in aqueous media even in substoichiometric amounts, i.e. in so-called threshold treatment.

A further possible use of the compounds according to the present invention is their use for producing liquid fertilizer preparations.

Of special importance is the exceptionally high solubility of the free acids in aqueous media. The solubility of most of the heretofore known amino phosphonic acids is much lower. For instance, the compounds described in the following examples have a solubility of at least 100 g. in 100 cc. of water.

In contrast to the extraordinarily high solubility of the novel N-substituted amino alkane phosphonic acids, the known unsubstituted amino alkane phosphonic acids have only a low solubility in water. The solubility of the following known amino phosphonic acids in water at 25° C. is, for instance, as follows:

Amino methane diphosphonic acid: 0.3%
1-Amino ethane-1,1-diphosphonic acid: 3.4%
Ethylene diamino tetramethylene phosphonic acid: 2.3%
Hexamethylene diamino tetramethylene phosphonic acid: 0.8%

It is interesting to note that the solubility of the phosphonic acids according to the present invention is even increased by the presence of small amounts of impurities, especially those present already in the starting materials and remaining in the novel amino phosphonic acids during their preparation.

DESCRIPTION OF THE PREFERRED EMBODIMENTS

The following examples serve to illustrate the present invention without, however, limiting the same thereto.

EXAMPLE 1

99.5 g. of amino methane diphosphonic acid are dissolved in 400 g. of a 20% sodium hydroxide solution. 66 g. of ethylene oxide are conducted into the resulting solution at such a speed that the temperature does not exceed 40° C. Thereafter, the reaction mixture is stirred for two hours at room temperature and is then heated to 80° C. for about one hour in order to complete the reaction. After concentrating the solution partly by evaporation in a vacuum preferably at a temperature between about 40° C. and about 60° C., methanol is added thereto in an amount sufficient to cause complete precipitation of the crystalline reaction product. Preferably twice the amount of methanol is added to the concentrated solution. The precipitated reaction product consists to 90% of the sodium salt of N,N-bis-(2-hydroxy ethane) amino methane diphosphonic acid or di-ethanol amino methane diphosphonic acid. The remainder is the sodium salt of N-(2-hydroxy ethane) amino methane diphosphonic acid.

The crystalline reaction product is converted into the free phosphonic acid by dissolving it in water and treating its aqueous solution with a cation exchange agent.

Analysis: Calculated: 21.52% C; 5.02% N; 22.19% P. Found: 21.1% C; 5.2% N; 22.8% P.

EXAMPLE 2

41 g. of amino ethane diphosphonic acid are added, while stirring, to a solution of 45 g. of potassium hydroxide in 150 cc. of water. After cooling the solution to room temperature, 9 g. of ethylene oxide are introduced thereinto within half an hour. Thereafter, the reaction mixture is stirred at room temperature for 2 hours and is heated to 80° C. for one hour in order to complete the reaction. The tripotassium salt of N-(2-hydroxy ethane)-1-amino ethane-1,1-diphosphonic acid is precipitated by adding methanol to the reaction mixture. The reaction product is purified by contacting its solution with a cation exchange agent and drying it in a vacuum at 80° C. to 100° C.

Yield: 86% of the theoretical yield.

Analysis: Calculated: 19.28% C; 5.62% N; 24.87% P. Found: 20.4% C; 4.9% N; 25.8% P.

When using, in place of ethylene oxide, 11 g. of trimethylene oxide and otherwise proceeding as described hereinabove, the tripotassium salt of N-(3-hydroxy propane)-1-amino ethane-1,1-diphosphonic acid is obtained.

EXAMPLE 3

20.5 g. of 1-amino ethane-1,1-diphosphonic acid are added to a solution of 16g. of sodium hydroxide in 150 cc. of water. 13 g. of glycidic acid amide or, respectively, 18 g. of glycidic acid ethyl ester, are added thereto while stirring vigorously. After continuing stirring at room temperature for 30 minutes, the temperature of the reaction mixture is gradually increased to 100° C. within about two hours. The reaction mixture is kept at said temperature for 30 minutes. The resulting solution is diluted with water to three times its volume and the diluted solution is treated with a cation exchange agent. After concentrating the thus purified and acidified solution by evaporation and adding ethanol thereto, N-(1,1-diphosphono ethane)-3-amino-2-hydroxy propionic acid is obtained.

Yield: 74% of the theoretical yield.

Analysis: Calculated: 20.49% C; 4.78% N; 21.13% P. Found: 19.8% C; 5.2% N; 22.1% P

EXAMPLE 4

45.6 g. of 2-carboxy-1-amino ethane-1,1-diphosphonic acid are dissolved in 160 g. of a 35% sodium hydroxide solution. After cooling, 11 g. of ethylene oxide are introduced into said solution in such a manner that the temperature does not exceed 40° C. The reaction mixture is stirred for two hours and heated to 80° C. for a short period of time. The sodium salt of 2-carboxy-N-2-hydroxy ethane-1-amino ethane-1,1-diphosphonic acid is precipitated from said solution by the addition of acetone. The substantially pure acid is obtained by treating the aqueous solution of the sodium salt with a cation exchange agent.

Analysis: Calculated 20.56% C; 4.80% N; 21.21% P. Found: 20.8% C; 4.9% N; 22.0% P.

EXAMPLE 5

95 g. of amino methane diphosphonic acid are dissolved in 400 g. of a 20% sodium hydroxide solution while stirring. 63 g. of 1,2-propylene oxide are added drop by drop to said solution at a temperature of 30° C. to 40° C. within one hour. The temperature of the reaction mixture is then maintained at 40° C. for 2 hours and the mixture is heated to 100° C. for 2 hours while stirring. After concentrating the resulting solution by evaporation in a vacuum, the sodium salt of N,N-bis-(2-hydroxy propane) amino methane diphosphonic acid is obtained. Said salt is contaminated with about 5% of the sodium salt of N-(2-hydroxy propane) amino methane diphosphonic acid. After treating the solution of said sodium salt with a cation exchange agent, a slightly yellowish colored compound is obtained.

Analysis: Calculated: 27.37% C; 4.56% N; 20.17% P.
Found: 26.2% C; 4.5% N; 20.6% P.

EXAMPLE 6

53.4 g. of benzylamino diphosphonic acid are added to a mixture of 44.8 g. of potassium hydroxide and 300 cc. of water while stirring. After cooling, 9.5 g. of ethylene oxide are introduced into said solution in such a manner that its temperature does not exceed 30° C. to 40° C. The reaction mixture is then stirred at 50° C. for 2 hours. The potassium salt of N-(2-hydroxy ethyl) benzylamino diphosphonic acid is obtained from the reaction solution by precipitation with methanol. The solution of the potassium salt is treated with a cation exchange agent and evaporated to dryness in a vacuum at 80° C.

Yield: 92% of the theoretical yield.

Analysis: Calculated: 34.74% C; 4.50% N; 19.91% P.
Found: 33.9% C; 4.7% N; 19.8% P.

EXAMPLE 7

55 g. of 1-amino propane-1,1-diphosphonic acid are dissolved in 200 g. of a 20% sodium hydroxide solution. 35.6 g. of 2,3-epoxy-1-propanol (glycidol) are gradually added thereto at room temperature while stirring. The temperature increases during said addition slowly to 45° C. The reaction mixture is then heated slowly to 100° C. and is kept at said temperature for 1 hour in order to complete the reaction. After cooling, the solution is concentrated by evaporation in a vacuum. The remaining viscous oil is stirred with ethanol for 3 to 4 hours. The solvent is removed by decanting and the free acid is obtained by treating the aqueous solution of the resulting salt with a cation exchange agent.

Analysis: Calculated: 29.44% C; 3.81% N; 16.87% P.
Found: 29.0% C; 3.9% N; 16.1% P.

EXAMPLE 8

102 g. of 1-amino ethane-1,1-diphosphonic acid are converted into the tetrasodium salt by dissolving the acid in 400 g. of a 20% sodium hydroxide solution. 73 g. of 2,3-epoxy-1-propanol (glycidol) are added thereto at 40° C. within 1 hour. The reaction mixture is heated to 100° C. for 2 hours. The resulting solution is concentrated by evaporation and the crystalline reaction product which consists of the sodium salt of N-(1,2-dihydroxy propane)-1-amino ethane-1,1-diphosphonic acid is washed with ethanol. The free acid is obtained by treating the solution of the sodium salt with a cation exchange agent.

Analysis: Calculated: 21.52% C; 5.02% N; 22.19% P.
Found: 22.3% C; 4.9% N; 21.7% P.

EXAMPLE 9

50 g. of 1-amino ethane-1,1-diphosphonic acid are dissolved in a solution of 40 g. of sodium hydroxide in 300 cc. of water. 58 g. of epichlorohydrin are added drop by drop thereto at 50° C. within one hour. The reaction mixture is stirred at said temperature for 1 hour and is boiled under reflux for two more hours in order to effect saponification. The reaction solution is passed through a cation exchange agent. The resulting solution is concentrated by evaporation. The N,N-bis-(1,2-dihydroxy propane)-1-amino ethane-1,1-diphosphonic acid is precipitated by the addition of a mixture of acetone and ethanol in the proportion of 1 : 1 to 1 : 2.

Yield: 79% of the theoretical yield.

Analysis: Calculated: 27.20% C; 3.97% N; 17.54% P.
Found: 28.5% C; 4.1% N; 17.2% P.

The yield of the novel N-hydroxy alkane amino alkane diphosphonic acids, when produced according to the process of the present invention, is between about 70% and about 95%.

Any commercial cation exchange agents can be used for converting the alkali metal salts into the corresponding free N-hydroxy alkane amino alkane diphosphonic acids. Suitable cation exchange agents are, for instance, those sold under the trademarks "DUOLITE", "LEWALIT", "AMBERLITE", and others.

The following examples serve to illustrate the manner in which the new N-hydroxy alkane amino alkane diphosphonic acids and their alkali metal salts are used on account of their high sequestering power such as for preventing scale and deposit formation in aqueous systems as they are employed, for instance, in bleaching, in water used for sterilizing cans, for preventing formation of resinous deposits in the manufacture of paper, and the like.

EXAMPLE 10

15 g. of desized cotton fabric of a starting degree of whiteness of 58.6, as determined with the "ELREPHO apparatus with filter R 46", and of a degree of polymerization value of 1842 are bleached with the compositions as given hereinafter in a laboratory equipment of the "Multicolor" type of the firm Pretema A.G. The proportion of fabric to bath was 1 to 20. Bleaching was effected at a temperature of 150° C. for 30 minutes (hot temperature process).

The composition of the bleaching baths was as follows:

Bleaching Bath A 5 cc./l. of 30% hydrogen peroxide, x cc./l. of a sodium hydroxide solution in an amount sufficient to adjust the pH-value of the bleaching bath to a pH of 12, 0.2 g./l. of N-(2-hydroxy-ethane)-1-amino ethane-1,1-diphosphonic acid.

Bleaching Bath B

The composition is the same as that of bleaching bath A but with the addition of 4 mg./l. of ferric ions to the aqueous bath.

Bleaching Bath C

The composition is the same as that of bleaching bath A but water of 5° German hardness (magnesium hardness) is used for making up the bleaching solution.

| | Bleaching Results: | |
|---|---|---|
| | Degree of Polymerization | Degree of Whiteness |
| Bleaching Bath A | 1500 | 75.3 |
| Bleaching Bath B | 1400 | 72.1 |
| Bleaching Bath C | 1580 | 75.3 |

It is evident from these tests that the degree of whiteness is very considerably increased while the degree of polymerization is reduced by only about 14% to about 24% although bleaching is effected at the high temperature of 150° C.

EXAMPLE 11

The following test was carried out in an upright autoclave of a capacity of 10 l. of water. The autoclave was operated at about 4 atmospheres gauge and at a temperature of 140° C. The autoclave was charged with conventional tin plate cans.

Tap water of the following composition was used for sterilization:
- Total degree of hardness: 25° German hardness
- Hardness due to carbonates: 17° German hardness
- Chlorides: 53 mg./l.
- Sulfates: 85 mg./l.
- Free carbon dioxide: 40 mg./l.
- Bound carbon dioxide: 125 mg./l.
- pH-value: 7.2

Before sterilization of the cans 5 cc. of N-(2-hydroxy ethane)-1-amino ethane-1,1-diphosphonic acid were added to the water. Addition of said phosphonic acid resulted in keeping not only the sterilized cans but also the autoclave free of incrustations. The cans had a glossy and shiny appearance.

EXAMPLE 12

250 kg. of bleached sulfite pulp known for its property of causing continuously difficulties on the paper machine due to resin deposition were beaten to a 3% suspension in water. The resulting stock suspension was ground in a Hollander beater to about 78° Schopper-Riegler, i.e. so as to form a well beaten pulp suitable for producing dense sheets of parchment-like paper. The pH-value of the resulting slurry was 6.0. Before starting beating, 0.5 kg. of the trisodium salt of N-(2-hydroxy ethane)-1-amino ethane-1,1-diphosphonic acid were added to the slurry in the Hollander beater. After beating and refining, 0.8 kg. of the same phosphonic acid were admixed thereto.

When proceeding in this manner, no resinous deposits were observed on the walls of the Hollander beater and also not on the pipe lines and subsequently on the paper machine.

The same or similar results as described in Examples 10 to 12 were observed when using other N-hydroxy alkane amino alkane diphosphonic acids as obtained, for instance, according to Examples 1 to 9.

Of course, many changes and variations in the process of preparing the novel N-hydroxy alkane amino alkane diphosphonic acid of the present invention and in their use as complex forming and sequestering agents, for preventing pitch formation during the manufacture of paper, cardboard, boxboard, and the like, and for other purposes can be made by those skilled in the art in accordance with the principles set forth herein and in the claims annexed hereto.

We claim:

1. A method of sequestering bivalent and polyvalent metal ions in an aqueous system, comprising the step of adding an effective sequestering amount of a compound of the formula

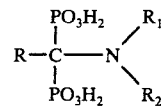

in which
R is hydrogen, lower alkyl, phenyl, hydroxy lower alkyl, or carboxy lower alkyl;
$R_1$ is hydrogen, lower alkyl, hydroxy lower alkyl, dihydroxy lower alkyl, or hydroxy carboxy lower alkyl, and
$R_2$ is hydroxy lower alkyl, or the alkali metal salts thereof, to said aqueous system in order to effect complex formation with said bivalent and polyvalent metal ions.

2. The method according to claim 1, said method comprising the step of adding a substoichiometric amount of said compound to an aqueous system in order to stabilize the water hardness therein.

3. In a process for treating an aqueous medium containing bivalent and polyvalent ions in a heating system used for the heat treatment of containers, said process comprising the step of adding to the aqueous heating medium in said heating system an effective complexing amount of a scale- and corrosion-suppressing N-hydroxy alkane amino alkane diphosphonic acid of the formula

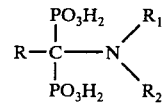

in which
R is hydrogen, lower alkyl, phenyl, hydroxy lower alkyl, or carboxy lower alkyl;
$R_1$ is hydrogen, lower alkyl, hydroxy lower alkyl, dihydroxy lower alkyl, or hydroxy carboxy lower alkyl, and
$R_2$ is hydroxy lower alkyl, or the alkali metal salts thereof, to said aqueous medium in order to effect complex formation with said bivalent and polyvalent metal ions.

* * * * *